(12) United States Patent
Lenna et al.

(10) Patent No.: US 8,933,061 B2
(45) Date of Patent: Jan. 13, 2015

(54) PROCESS FOR THE PREPARATION OF DROSPIRENONE

(75) Inventors: Roberto Lenna, S. Giorgio Su Legnano (IT); Francesco Barbieri, Bovisio Masciago (IT); Daniele Giudici, Caronno Pertusella (IT)

(73) Assignee: Industriale Chimica S.r.l., Milan (IT)

( * ) Notice: Subject to any disclaimer, the term of this patent is extended or adjusted under 35 U.S.C. 154(b) by 206 days.

(21) Appl. No.: 13/553,509

(22) Filed: Jul. 19, 2012

(65) Prior Publication Data

US 2013/0030169 A1 Jan. 31, 2013

(30) Foreign Application Priority Data

Jul. 25, 2011 (IT) .......................... MI2011A001383

(51) Int. Cl.
*A61K 31/585* (2006.01)
*C07J 53/00* (2006.01)

(52) U.S. Cl.
CPC .................................. *C07J 53/008* (2013.01)
USPC .......................................... 514/173; 540/15

(58) Field of Classification Search
CPC ...... A61K 31/34; C07D 307/94; C07J 53/008
USPC ........................................... 514/173; 540/15
See application file for complete search history.

(56) References Cited

FOREIGN PATENT DOCUMENTS

| EP | 0075189 | 3/1983 |
|----|---------|--------|
| EP | 1828222 B1 | 12/2010 |
| WO | 2006/061309 | 6/2006 |
| WO | 2007009821 | 1/2007 |

OTHER PUBLICATIONS

EP Search Report, IT Application No. MI20111383, Mar. 21, 2012.
Wertz, S. et al, "Hydroxylamine as a Source for Nitric Oxide in Metal-Free 2,2,6,6-Tetramethylpiperidine N-Oxyl Radical (TEMPO) Catalyzed Aerobic Oxidation of Alcohols", Advanced Synthetic Catalyst, No. 353, pp. 69-72, 2011.
Yang, G. et al, "In situ Formation of NOx and Br Anion for Aerobic Oxidation of Benzylic Alcohols without Transition Metal", Synlett, No. 3, pp. 437-440, 2010.

*Primary Examiner* — Brenda Coleman
(74) *Attorney, Agent, or Firm* — Fish & Tsang LLP

(57) ABSTRACT

A process is described, comprising the oxidation of 17α-(3-hydroxypropyl)-6β,7β,15β,16β-dimethylen-5β-androstan-3β,5,17β-triol, for the preparation of drospirenone, a synthetic steroid with progestogenic, antimineralocorticoid and antiandrogenic activity, useful for preparing pharmaceutical compositions with contraceptive action.

14 Claims, No Drawings

PROCESS FOR THE PREPARATION OF DROSPIRENONE

PRIORITY

This application claims priority to Italian Patent Application No. MI2011A001383 filed on Jul. 25, 2011 which is incorporated herein by reference in its entirety.

FIELD OF THE INVENTION

The present invention relates to the field of processes for the synthesis of steroids, in particular a process for the preparation on industrial scale of drospirenone.

STATE OF THE ART

The compound of formula (I) shown below, whose chemical name is 6β,7β;15β,16β-dimethylen-3-oxo-17α-pregn-4-ene-21,17-carbolactone, is commonly referred to with the name drospirenone:

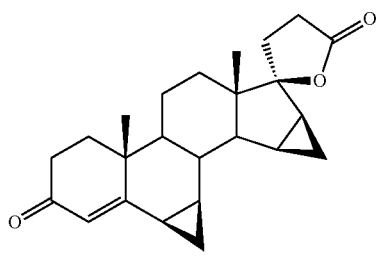

(I)

Drospirenone is a synthetic steroid with progestogenic, antimineralocorticoid and antiandrogenic activity; thanks to these characteristics, it is used from some time now to prepare pharmaceutical compositions with contraceptive action for oral administration.

In literature, several processes for the preparation of drospirenone are known.

The process described in European Patent EP 075189 B1 obtains the final product drospirenone through oxidation under heating of 17α-(3-hydroxypropyl)-6β,7β;15β,16β-dimethylen-5β-androstan-3β,5,17β-triol with a pyridine/water/chromic anhydride mixture. This step constitutes a substantial disadvantage of the process: in fact, chromic anhydride, as all the compounds of Cr(VI), is an ascertained carcinogen, the use of which is subject to such legislative restrictions that the precautions required during use and the disposal of these products, make them practically unusable.

Another process for the preparation of drospirenone is described in European Patent 918791 B8; in the process of this document drospirenone is obtained, again starting from 17α-(3-hydroxypropyl)-6β,7β;15β,16β-dimethylen-5β-androstan-3β,5,17β-triol, in two distinct phases and by using ruthenium salts as oxidants, which necessarily must then be completely eliminated from the product.

European Patent EP 1828222 B1 discloses a further process, in which the oxidation step is carried out by using as oxidant calcium hypochlorite, which is added to the reaction in portions until completion of the transformation. This process overcomes the disadvantages of the prior art since calcium hypochlorite is not a carcinogenic reagent nor is it a derivative of ruthenium; however, the need for subsequent additions of reactive and the analytical controls in the course of reaction, although simple, are a hindrance to a standardized production that must proceed continuously or nearly so. Consequently, even the method of this patent has process drawbacks, which it is preferable to avoid in an industrial production.

It is therefore still felt the need for a simple process which allows to overcome the drawbacks of the prior art.

The purpose of the present invention is therefore to provide an industrial process which allows to prepare drospirenone by avoiding the use of dangerous reagents or the use of which is in any case restricted by rules of the sector, and by minimizing the interventions of the operators during the same process.

SUMMARY OF THE INVENTION

This object is achieved with the present invention, which relates to a process for the production of drospirenone comprising the oxidation of the compound 17α-(3-hydroxypropyl)-6β,7β,15β,16β-dimethylen-5β-androstan-3β,5,17β-triol of formula (II) with gaseous oxygen in a not oxidisable organic solvent, in the presence of 2,2,6,6-tetramethylpiperidine-1-oxyl radical or a derivative thereof and of hydroxylamine (in the form of free base), said oxidation being followed by the addition of a protic acid directly in the same container where the oxidation has taken place, to obtain the drospirenone of formula (I) (reaction schema 1):

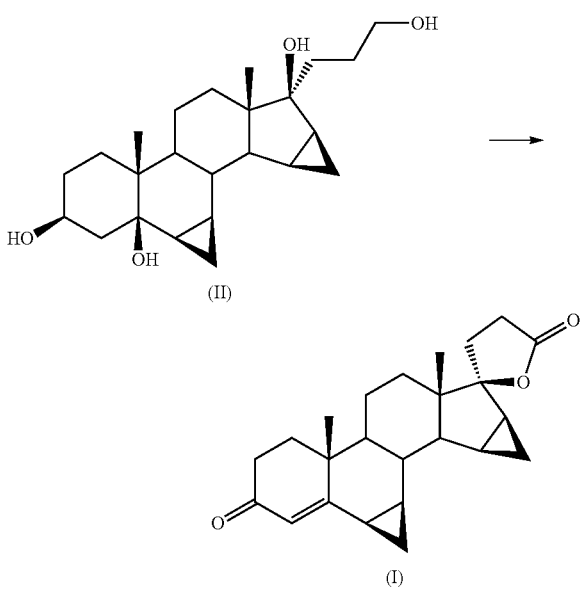

The reaction of the schema shown above passes through the formation of the compound 6β,7β-15β,16β-dimethylen-5β-hydroxy-3-oxo-17α-pregn-21,17-carbolactone (compound (III)), which has a hydroxyl in position 5 of the steroid skeleton:

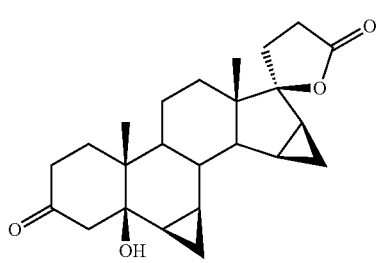

(III)

this compound is then transformed into drospirenone through dehydration and subsequent formation of the double bond between positions 4 and 5 of the same skeleton; this intermediate compound is commonly referred to in the field as 5-OH-drospirenone, and is formed by oxidation of compound (II) in equilibrium with drospirenone, into which is then converted quantitatively by addition of the protic acid.

The conversion into drospirenone of the intermediate (II) portion present in the reaction mixture does not require separation or purification from the other components thereof.

The characteristics and the advantages of the present process are illustrated in detail in the following description.

DETAILED DESCRIPTION

The Applicant has developed a new process, extremely simple, which allows obtaining drospirenone by using oxygen as oxidizing agent, in the presence of a catalytic system consisting of 2,2,6,6-tetramethylpiperidine-1-oxyl radical or of one of its derivatives and hydroxylamine, $NH_2OH$. Compound 2,2,6,6-tetramethylpiperidine-1-oxyl radical is known in the field with the abbreviation TEMPO, which will be used hereinafter.

The oxidation of alcohols with TEMPO, hydroxylamine and oxygen was recently described in the article "Hydroxylamine as a Source for Nitric Oxide in Metal-Free 2,2,6,6-Tetramethylpiperidine N-Oxyl Radical (TEMPO) Catalyzed Aerobic Oxidation of Alcohols", S. Wertz and A. Studer, Adv. Synth. Catal. 2011, vol. 353, pages 69-72.

However, by reading this article an expert of steroids chemistry would have been directed not to use this oxidation system in the reaction of the present invention. In fact, the cited article shows that the oxidation in the studied conditions leads to very different yield values depending on the starting substrate; according to this article, the oxidation of primary and secondary benzyl alcohols (examples 1-8) and non benzyl linear primary alcohols (examples 9-12) takes place with high yields; vice versa, the oxidation to cyclohexanone of cyclohexanol (example 13), i.e. an alcohol in which the hydroxyl is on a carbon that is part of a cyclic structure (such as in steroids) and relatively sterically hindered, provides a low yield of 21% of recovered product, even with longer reaction times.

As shown in the reaction schema shown below, it envisages three oxidations of alcohol groups (reactions A, B and D) and a cyclisation (reaction C):

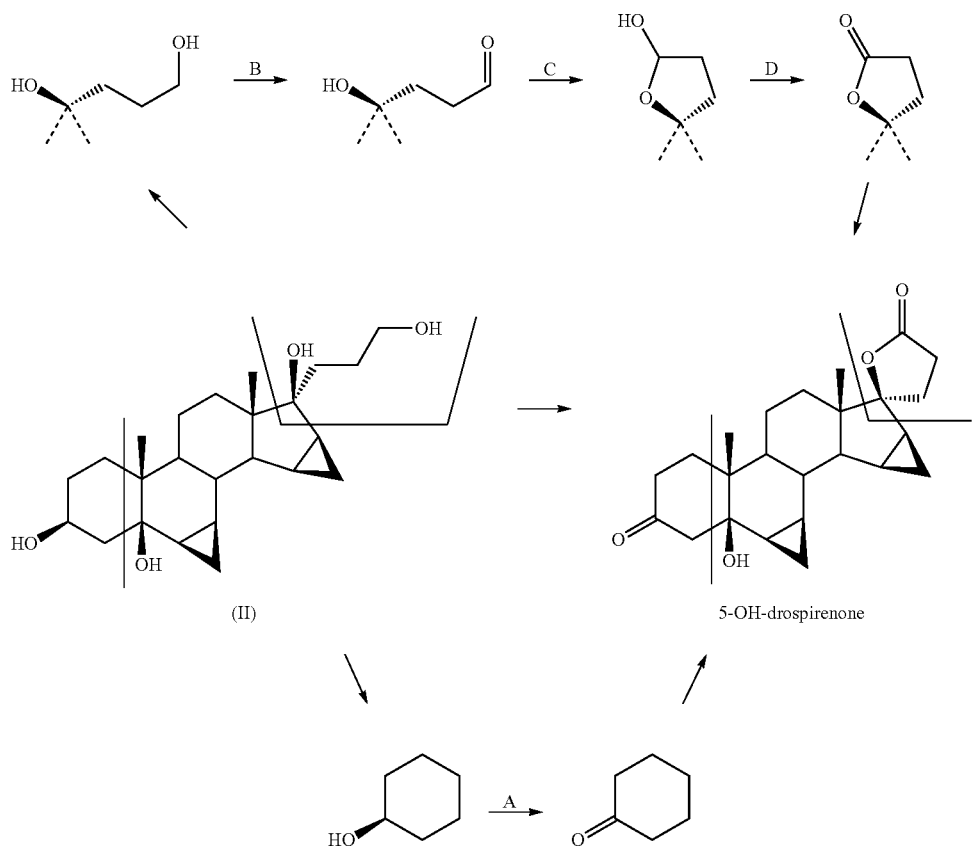

Oxidation A is equivalent to the reaction of example 13 of aforementioned article, of 21% yield; the example of the article most similar to oxidation B is number 11, of 87% yield; finally, even if in the article does not exist an example related to the oxidation of a lactol, as in oxidation D given above, this is assimilable to reaction A. Since the overall yield of a reaction is obtained by multiplying the yields of the single steps, by reading the article, the person skilled in the field would have expected just a very small yield equal to 0.21× 0.87=0.19 for the combination of reactions A and B, which would have dropped further to expected values around 5% taking into consideration also reaction D. Furthermore, it is known that the reactivity of the functional groups present on the skeleton of steroids is lower with respect to that of the same functional groups in aliphatic compounds, due to the rigidity of the skeleton, which limits the degree of freedom of the involved functional groups. Accordingly, by reading the cited article, the person skilled in the field would have expected for the oxidation of compound (II) to drospirenone a yield lower than 5%, namely, that the desired product would have been obtained as an impurity and certainly not as a main product.

Furthermore, by reading the article, the skilled person of the field would have learned that the reaction is very sensitive to the solvent, and that the oxidation does not take place in solvents such as α,α,α-trifluorotoluene, a water/acetonitrile mixture or a water phosphate buffer solution, and that therefore the choice of a "wrong" solvent would have led to zero the yield, already expected low, of the overall reaction; the solvents described as useful in the article are methylene chloride and 1,2-dichloroethane (DCE), but the latter is known to be carcinogenic.

The inventors have instead found that the reaction from compound (II) to drospirenone, under the conditions of the present invention, proceeds with yields around 50%, suitable for an industrial application of the process.

Unlike what is described in European Patent EP 1828222 B 1, in the present invention the reagents are loaded into the reaction container in a single addition, without the need for further actions in the course of the reaction.

The oxidation substrate of the present process, namely 17α-(3-hydroxypropyl)-6β,7β,15β,16β-dimethylen-5β-androstan-3β,5,17β-triol, may be obtained starting from commercial products by means of procedures known to any skilled person in the field. Preferably, this product is obtained according to the procedure described in steps a) to f) of patent EP 1828222 B 1. 17α-(3-hydroxypropyl)-6β,7β,15β,16β-dimethylen-5β-androstan-3β,5,17β-triol will also be referred to simply as "triol (II)" in the following description and in the examples.

The gaseous oxygen can be fed in the reaction container as pure oxygen, air, or a synthetic mixture of oxygen with an inert gas (for example the so-called synthetic air, widely used in the medical field).

As previously said, as a first component of the catalytic system, it is possible to use the compound known as TEMPO or its derivatives; the derivatives of the TEMPO, of possible use in the process of the present invention, are for example selected among 4-hydroxy-2,2,6,6-tetramethylpiperidine-1-oxyl radical, 4-methoxy-2,2,6,6-tetramethylpiperidine-1-oxyl radical, 4-(benzoyloxy)-2,2,6,6-tetramethylpiperidine-1-oxyl radical, 4-acetamido-2,2,6,6-tetramethylpiperidine-1-oxyl radical and 4-amino-2,2,6,6-tetramethylpiperidine-1-oxyl radical.

For the aims of the invention, useful molar amounts of TEMPO or the derivative thereof are comprised between 0.1 times and 3 times the moles of the triol (II) to be oxidized (molar ratio TEMPO/triol (II) comprised between 0.1 and 3).

The second component of the catalytic system is hydroxylamine ($NH_2OH$) which, for the aims of the invention, is added to the reaction mixture in an amount comprised between 0.2 times and 6 times the moles of the triol (II) to be oxidized (molar ratio $NH_2OH$/triol (II) comprised between 0.2 and 6). Hydroxylamine is preferably used in the form of an aqueous solution with a concentration ranging between 45 and 55%, more preferably 50%, by weight.

As organic solvent for the oxidation reaction, can be used a solvent selected from the group consisting of ethers, such as methyl t-butyl ether and tetrahydrofuran, esters, such as ethyl acetate, hydrocarbons, e.g. toluene, halogenated hydrocarbons, such as methylene chloride, acetone and mixtures thereof.

The oxidation reaction can be carried out at a temperature between 50 and 110° C., and preferably between 60 and 90° C., for a time between 2 and 20 hours, preferably between 3 and 6 hours.

Preferred conditions of the oxidation reaction are: pure oxygen as oxidizing agent, methylene chloride as organic solvent, temperature of 80° C., use of 2,2,6,6-tetramethylpiperidine-1-oxyl radical in a molar ratio to triol (II) comprised between 0.15 and 0.25, and of a aqueous solution of hydroxylamine (50% by weight) in a molar ratio $NH_2OH$/triol (II) comprised between 0.2 and 0.45, for a duration of 4 hours.

At the end of the oxidation reaction, a protic acid is added to the reaction mixture, pure or in solution in an organic solvent; alternatively, the organic solution in which the oxidation reaction took place is distilled until a semi-solid residue is obtained, which is redissolved in a suitable organic solvent, and the protic acid is added to the solution thus obtained. The protic acid is selected for example from the group consisting of concentrated hydrochloric acid, diluted hydrochloric acid, and p-toluenesulfonic acid; preferably, the protic acid used is p-toluenesulfonic monohydrated acid. The purpose of the addition of the protic acid is to transform the part of the 5-OH-drospirenone compound formed in the oxidation reaction, and in equilibrium with the drospirenone, in the final compound.

The crude drospirenone obtained with the present process may be purified with techniques known to skilled persons in the art and described in publications and patents.

The invention will be further illustrated by the following examples, given by way of illustration and not limiting to the present invention. The reagents used in the examples are of common commercial availability and are used without prior purification needs. All concentrations are expressed as percentages by weight unless otherwise specified. In the examples, the following abbreviations are used:

DRSP=drospirenone;
5-OH-DRSP=5-OH-drospirenone;
PTSA=p-Toluenesulfonic acid;
THF=tetrahydrofuran.

EXAMPLE 1

In a 250 ml reactor for reactions under pressure, are loaded 5 g of crude triol (II) (0.0128 mol) in 40 ml of tetrahydrofuran and 80 ml of methylene chloride.

5.1 g of 50% hydroxylamine aqueous solution (0.0773 mol) and 6 g of TEMPO (0.0385 mol) are added, keeping the temperature at 20/25° C.

The system is brought to 6 bar with pure oxygen and stirred at 80° C. for 4 hours.

The progress of the reaction is monitored by means of TLC by which it is detected the disappearance of the starting product and the formation of DRSP and 5-OH-DRSP as main products (comparison with samples of the pure compounds obtained by methods known in the field).

The residue, obtained by evaporation of the solvent, is taken up with 100 ml of methylene chloride.

The solution is washed with water until pH>6 (the pH of the aqueous phase of the first washing is about 4), then the solvent is eliminated under reduced pressure.

The product thus obtained, after purification by chromatography (2.6 g), is re-checked by HPLC that confirms the presence of DRSP and 5-OH-DRSP.

The weight ratio between the two, of 1.25/1 in favour of DRSP, is determined by chromatographing a homogeneous portion of the mixture and by weighing the two products isolated and dried to constant weight.

In addition, a 100 mg sample of the mixture is oxidized as described in patent EP 0 075 189, example H.

A second 100 mg sample of the mixture is treated, in THF, with PTSA.

The products obtained by the two reactions are identified, by means of HPLC, as DRSP.

EXAMPLE 2

5 g of crude triol (II) (0.0128 mol) are loaded into a 250 ml reactor for pressure reactions, in 40 ml of THF and 80 ml of methylene chloride.

253.44 mg of aqueous hydroxylamine solution at 50% (0.00384 mol) and 400 mg of TEMPO (0.00256 mol) are added, maintaining the temperature at 20/25° C.

The system is brought to 6 bar with pure oxygen then heated at 80° C. for 4 hours.

The progress of the reaction is monitored by TLC, which reveals the disappearance of the starting product and the formation of DRSP and 5-OH-DRSP as main products (comparison with samples of the pure compounds).

The reaction solution is left at room temperature for 20 hours, then 20 ml of said solution is dry concentrated obtaining a residue of 850 mg, which re-tested in TLC confirms the presence of DRSP and 5-OH-DRSP.

EXAMPLE 3

In a 250 ml reactor for reactions under pressure, are loaded 5 g of crude triol (II) in 40 ml of THF and 80 ml of methylene chloride.

250 mg of 50% hydroxylamine aqueous solution and 400 mg of TEMPO are added, keeping the temperature at 20/25° C.

The system is brought to 12 bar with pure oxygen, then it is heated at 80° C. for 4 hours.

The progress of the reaction is monitored by means of TLC by which it is observed the disappearance of the starting product and the formation of DRSP and 5-OH-DRSP as main products (comparison with samples of the pure compounds).

The organic solution (120 ml) is added with 300 mg of PTSA (pH 1) and is left under stirring at room temperature overnight.

The solution is washed with water, dried with sodium sulfate and the solvent is eliminated under reduced pressure.

5 g of crude residue are obtained which, controlled in HPLC, appear to be DRSP with a 68.3% purity.

EXAMPLE 4

In a 250 ml reactor for reactions under pressure, are loaded 5 g of crude triol (II) in 40 ml of THF and 80 ml of methylene chloride.

250 mg of 50% hydroxylamine aqueous solution and 400 mg of TEMPO are added, keeping the temperature at 20/25° C.

The system is brought to 3 bar with pure oxygen, then it is heated at 80° C. for 4 hours.

The progress of the reaction is monitored by means of TLC by which it is observed the presence of the starting product (triol (II)) and the formation of 5-OH-DRSP and DRSP (comparison with samples of the pure compounds).

EXAMPLE 5

In a 250 ml reactor for reactions under pressure, are loaded 5 g of crude triol (II) in 120 ml of methylene chloride.

250 mg of 50% hydroxylamine aqueous solution and 400 mg of TEMPO are added, keeping the temperature at 20/25° C.

The system is brought to 6 bar with pure oxygen, then it is heated at 80° C. for 4 hours.

The progress of the reaction is monitored by means of TLC by which it is observed the disappearance of the starting product and the formation of 5-OH-DRSP (prevalent) and DRSP as main products (comparison with samples of the pure compounds).

EXAMPLE 6

In a 250 ml reactor for reactions under pressure, are loaded 5 g of crude triol (II) in 240 ml of methylene chloride.

250 mg of 50% hydroxylamine aqueous solution and 400 mg of TEMPO are added, keeping the temperature at 20/25° C.

The system is brought to 6 bar with pure oxygen and heated at 80° C. for 4 hours.

The progress of the reaction is monitored by means of TLC by which it is observed the almost total disappearance of the starting product and the formation of 5-OH-DRSP (prevalent) and DRSP as main products (comparison with samples of the pure compounds).

EXAMPLE 7

In a 250 ml reactor for reactions under pressure, are loaded 10 g of triol (II) (previously purified by hot filtration from acetonitrile) in 240 ml of methylene chloride.

500 mg of 50% hydroxylamine aqueous solution and 800 mg of TEMPO are added, keeping the temperature at 20/25° C.

The system is brought to 6 bar with pure oxygen and then heated at 80° C. for 4 hours.

The progress of the reaction is monitored by means of TLC by which it is observed the formation of DRSP and 5-OH-DRSP (prevalent) as main products (comparison with samples of the pure compounds).

The organic solution (240 ml) is divided into three 80 ml portions (A, B, C). To portion A are added 400 mg of PTSA and it is stirred at room temperature for 20 hours.

Portion B is washed with water until a neutral pH is obtained, dried, acidified (200 mg of PTSA) and stirred for 20 hours (at room temperature).

Portion C is washed with water until a neutral pH is obtained and dried (sodium sulfate).

The solvent is evaporated and the residue is taken up with 80 ml of THF and with 200 mg of PTSA.

The mixture is stirred at room temperature for 20 hours.

The solvent is eliminated under reduced pressure and the residue taken up with 80 ml of methylene chloride.

The three methylene solutions are washed with water until a neutral pH is obtained, dried (sodium sulfate) and evaporated at reduced P.

3.2 g of product from portion A, 3.2 g of product from portion B and 3.1 g of product from portion C are obtained, respectively, which are all controlled by HPLC.

The chromatograms confirm the absence of intermediate 5-OH-DRSP in the DRSP samples.

A portion of 2.8 g of sample C is chromatographed on silica gel (heptane-ethyl acetate gradient) and crystallized by acetone-isopropyl ether, obtaining 1.45 g of DRSP with HPLC purity greater than 98% (UV detector at 245 nm).

EXAMPLE 8

In a 250 ml reactor for reactions under pressure, are loaded 5 g of crude triol (II), in 120 ml of methylene chloride.

254 mg of 50% hydroxylamine aqueous solution and 400 mg of TEMPO are added, keeping the temperature at 20/25° C.

The system is brought to 6 bar with pure oxygen and it is stirred at 80° C. for 4 hours.

The organic solution is washed with water (two 60 ml washes), the organic phase is filtered with sodium sulfate and the solvent is eliminated at reduced pressure obtaining 4.4 g of crude product.

A portion of the crude product (1 g) is chromatographed on silica gel eluting with the ethyl acetate-heptane isomers mixture (gradient from 5% to 50% of ethyl acetate) obtaining 520 mg of product in which the DRSP/5-OH-DRSP ratio is 0.24 (ratio obtained by HPLC titles).

EXAMPLE 9

In a 250 ml reactor for reactions under pressure, are loaded 5 g of crude triol (II), in 120 ml of methylene chloride.

253.44 mg of 50% hydroxylamine aqueous solution and 400 mg of TEMPO are added, keeping the temperature at 20/25° C.

The system is brought to 10 bar with air and then it is heated at 80° C. for 5 hours.

The progress of the reaction is monitored by means of TLC by which it is observed the disappearance of the starting product and the formation of 5-OH-DRSP (main product) and a minority proportion of DRSP (comparison with samples of the pure compounds).

The invention claimed is:

1. A process for the preparation of drospirenone, comprising the oxidation of 17α-(3-hydroxypropyl)-6β,7β,15β,16β-dimethylene-5β-androstan-3β,5,17β-triol of formula (II) with an oxidizing agent in an organic solvent in the presence of 2,2,6,6-tetramethylpiperidine-1-oxyl radical or of a derivative thereof and of hydroxylamine, said oxidation being followed by the addition of a protic acid, directly into the vessel where oxidation occurred, to complete the formation of drospirenone of formula (I)

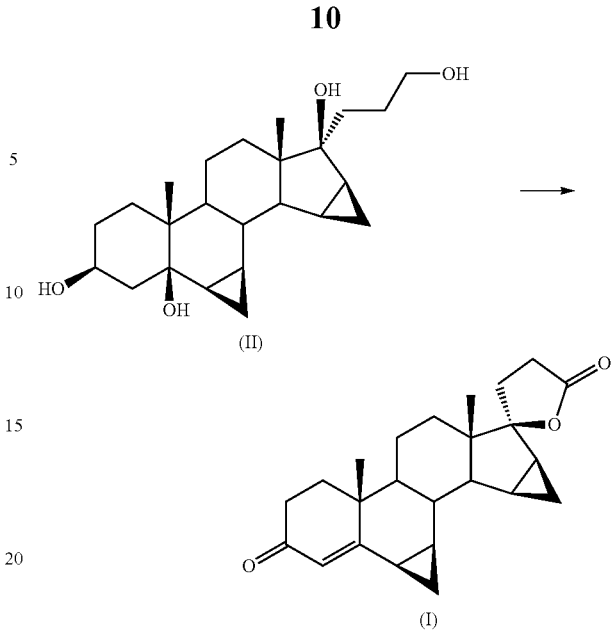

characterized in that said oxidizing agent is chosen from the group consisting of oxygen, mixtures of inert gas and oxygen, and air, and wherein said derivative of 2,2,6,6-tetramethylpiperidine-1-oxyl radical is chosen from the group consisting of 4-hydroxy-2,2,6,6-tetramethylpiperidine-1-oxyl radical, 4-methoxy-2,2,6,6-tetramethylpiperidine-1-oxyl radical, 4-(benzoyloxy)-2,2,6,6-tetramethylpiperidine-1-oxyl radical, 4-acetamido-2,2,6,6-tetramethylpiperidine-1-oxyl radical, and 4-amino-2,2,6,6-tetramethylpiperidine-1-oxyl radical.

2. The process according to claim 1, wherein said oxidizer is pure oxygen.

3. The process according to claim 1, wherein said organic solvent is chosen from the group consisting of acetone, toluene, methyl tert-butyl ether, ethyl acetate, methylene chloride, tetrahydrofuran, 1,2-dichloroethane and mixtures thereof.

4. The process according to claim 1, wherein said oxidation is carried out at a temperature of between 50 and 110° C.

5. The process according to claim 4, wherein said oxidation is carried out at a temperature of between 60 and 90° C.

6. The process according to claim 1, wherein the organic solvent is methylene chloride.

7. The process according to claim 1, wherein the mixture of solvents is tetrahydrofuran-methylene chloride.

8. The process according to claim 1, wherein the hydroxylamine is used in the form of an aqueous solution containing 45-55% by weight of hydroxylamine.

9. The process according to claim 1, wherein the gas before heating is charged under a pressure of between 3 and 12 bar.

10. The process according to claim 1, wherein the molar ratio between the 2,2,6,6-tetramethylpiperidine-1-oxyl radical and/or one of said derivatives and the 17α-(3-hydroxypropyl)-6β,7β,15β,16β-dimethylene-5β-androstan-3β,5,17β-triol to be oxidized is comprised between 0.1 and 3.

11. The process according to claim 10, wherein said molar ratio is comprised between 0.15 and 0.25.

12. The process according to claim 1, wherein the molar ratio between hydroxylamine and the 17α-(3-hydroxypropyl)-6β,7β,15β,16β-dimethylene-5β-androstan-3β,5,17β-triol to be oxidized is comprised between 0.2 and 6.

13. The process according to claim 12, wherein said molar ratio is comprised between 0.2 and 0.45.

14. The process according to claim 1, wherein, prior to the addition of the acid, both drospirenone and 5-OH-drospirenone are already present in quantities such that the minority component is at least 20% of the other component.

* * * * *